United States Patent
Nandi et al.

(10) Patent No.: US 11,583,521 B2
(45) Date of Patent: *Feb. 21, 2023

(54) LONG-ACTING INJECTION DOSAGE FORM OF BETA 3 ADRENORECEPTOR AGONISTS

(71) Applicant: Jubilant Pharma Holdings Inc., Yardley, PA (US)

(72) Inventors: Indranil Nandi, Yardley, PA (US); Tusharmouli Mukherjee, Yardley, PA (US)

(73) Assignee: Jubilant Pharma Holdings Inc., Yardley, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/364,469

(22) Filed: Jun. 30, 2021

(65) Prior Publication Data

US 2022/0000843 A1 Jan. 6, 2022

Related U.S. Application Data

(60) Provisional application No. 63/047,021, filed on Jul. 1, 2020.

(51) Int. Cl.
*A61K 31/426* (2006.01)
*A61K 47/02* (2006.01)
*A61K 47/26* (2006.01)
*A61K 47/38* (2006.01)
*A61K 9/00* (2006.01)

(52) U.S. Cl.
CPC .......... *A61K 31/426* (2013.01); *A61K 9/0019* (2013.01); *A61K 47/02* (2013.01); *A61K 47/26* (2013.01); *A61K 47/38* (2013.01)

(58) Field of Classification Search
None
See application file for complete search history.

(56) References Cited

U.S. PATENT DOCUMENTS

| | | | | |
|---|---|---|---|---|
| 4,853,375 A | * | 8/1989 | Krupin | A61K 31/65 514/152 |
| 8,772,315 B2 | * | 7/2014 | Suzuki | A61K 31/426 514/305 |
| 2002/0001586 A1 | * | 1/2002 | Liau | C12N 15/1072 424/155.1 |
| 2004/0072735 A1 | * | 4/2004 | Richon | A61P 31/04 514/575 |
| 2006/0015264 A1 | * | 1/2006 | McShea | C12N 15/111 702/20 |
| 2009/0143349 A1 | * | 6/2009 | Lewbart | A61P 29/00 514/182 |
| 2009/0163519 A1 | * | 6/2009 | Vermeulen | A61P 25/18 514/259.41 |
| 2013/0058930 A1 | * | 3/2013 | Dave | A61P 43/00 424/134.1 |
| 2014/0206729 A1 | * | 7/2014 | Peddy | A61P 13/00 514/370 |
| 2015/0031734 A1 | * | 1/2015 | Kasashima | A61K 9/1635 514/370 |
| 2019/0083402 A1 | * | 3/2019 | Talley | A61K 47/10 |

FOREIGN PATENT DOCUMENTS

| | | | | |
|---|---|---|---|---|
| EP | 3360866 A1 | * | 8/2018 | ............. A61P 13/10 |
| WO | WO-2018063963 A1 | * | 4/2018 | ........... A61K 38/063 |

OTHER PUBLICATIONS

Irby et al. Mol Pharm May 1, 2017; 14(5): 1325-1338. (Year: 2017).*

* cited by examiner

*Primary Examiner* — Katherine Peebles
(74) *Attorney, Agent, or Firm* — William D. Hare; McNeely, Hare & War, LLP

(57) ABSTRACT

Provided herein are the long-acting injection compositions of β3 adrenoreceptor agonists like mirabegron or their pharmaceutically acceptable salts or esters thereof. The present invention also relates to methods for preparing long-acting injection compositions and methods of using these dosage forms for the treatment of obesity, metabolic diseases, and other diseases as described herein. The long-acting injection compositions as per the present invention have desirable pharmaceutical technical attributes.

13 Claims, No Drawings

LONG-ACTING INJECTION DOSAGE FORM OF BETA 3 ADRENORECEPTOR AGONISTS

FIELD OF THE INVENTION

The present invention relates to long-acting parenteral dosage forms of β3 adrenoreceptor agonists or their pharmaceutically acceptable salts or solvates or esters thereof. The present invention also relates to methods for preparing these long-acting parenteral dosage forms and methods of using these dosage forms for the treatment of obesity, metabolic diseases, and other diseases as described herein.

BACKGROUND OF THE INVENTION

Obesity is becoming a growing concern in modern life due to its negative health effects on individual life. Obesity may be defined as abnormal or excessive fat accumulation that may impair health and body normal functions. Body mass index (BMI) is one of the index which is used as an indicator to define the measure of obesity in adults. Obesity is associated with increased risk of morbidity and mortality due to its associated chronic diseases such as metabolic diseases, hypertension, diabetes, patients at risk of having diabetes (pre-diabetes), cardiovascular diseases, hyperglycemia, gallbladder diseases, and even some types of cancer.

As a treatment option for obesity, both surgical and non-surgical methods are available. Surgical procedures in the treatment of obesity include various procedures such as biliopancreatic diversion, adjustable gastric banding, vertical banded gastroplasty, gastric plications, gastrostomies (stomach portion removal), stomach stapling and gastric and intestinal bypasses, and like. However, such surgical procedures involve a variety of complications and risks, during surgery as well as post-surgery.

Under non-surgical methods, the first line of treatment is to offer diet and lifestyle advice to patients such as reducing the fat content of their diet and increasing their physical activity. However, many patients find this difficult and need additional help from drug therapy to maintain results from these efforts. Currently, many drug therapies are approved by the United States Food and Drug Administration (USFDA) for the treatment of obesity such as orlistat, lorcaserin, liraglutide, phentermine hydrochloride, phentermine-topiramate combination, and naltrexone-bupropion combination. These drug therapies usually work with their associated mechanism of action such as reducing the amount of fat absorption from food, acting on the serotonin receptors, decreasing energy intake by suppressing appetite through stimulating the central nervous system, etc. However, these drug therapies do not provide long-term benefits and are accompanied by potentially harmful side effects. Thus, other efficient alternative approaches to overcome obesity are a need of an hour.

One area of focus for the treatment of obesity can be the promotion of energy expenditure through activation of a β3-adrenergic receptor on brown adipocytes. There are two types of adipose tissue that exist in mammals, white adipose tissue (WAT), which is specialized in the storage of excessive triglycerides, and brown adipose tissue (BAT), which plays a central role in metabolizing glucose, fatty acids, and other chemicals to produce heat. The activation of brown adipose tissue (BAT) can increase energy expenditure which makes brown adipose tissue (BAT) a promising new target for obesity and other metabolic diseases including type 2 diabetes. However, none of the anti-obesity drugs including β3-adrenergic receptor agonists have been approved in the USA for the treatment of obesity and its related metabolic disorders through stimulating brown adipose tissue (BAT) activity.

Mirabegron is one of the β3-adrenergic receptor agonist approved for the treatment of overactive bladder and its associated symptoms. Presently, Mirabegron is approved in the form of solid oral dosage forms in the US market as extended-release tablets in strengths of 25 mg and 50 mg. Mirabegron is chemically known as (R)-2-(2-aminothiazol-4-yl)-4'-{2-[(2-hydroxy-2 phenylethyl)amino] ethyl}acetanilide. It is represented with the following chemical structure:

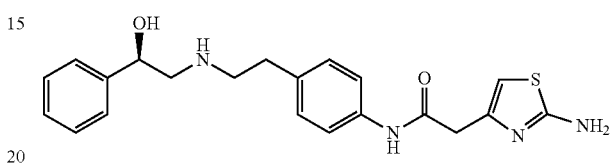

Mirabegron compound is disclosed in U.S. Pat. No. 6,346,532. Further, U.S. Pat. No. 10,842,780 disclose sustained-release, hydrogel-forming oral formulations of mirabegron. U.S. Pat. No. 8,835,474 and RE44,872 disclose methods of using mirabegron for the treatment of overactive bladder (OAB). U.S. Pat. No. 8,772,315 disclose combinations of mirabegron and solifenacin and methods of using such combinations for the treatment of OAB.

The use of β3-adrenergic receptor agonists including mirabegron in the treatment of obesity and metabolic disease is known in the literature. Effect of mirabegron to stimulate the activity of brown adipose tissue (BAT) thermogenesis was recently disclosed in 2015 (Cypess et al., "Activation of human brown adipose tissue by a beta3-adrenergic receptor agonist," *Cell metabolism* 21:33-38 (2015)). Since then, the clinical use of mirabegron and other β3-adrenergic receptor agonists in the treatment of obesity and its related metabolic disorders has become a topic of interest.

However, till date, no β3-adrenergic receptor agonist is approved in the USA market for the treatment of obesity, fat reduction/removal, and its related metabolic disorders. Moreover, the determination of critical parameters of various clinical candidates or molecules associated with drug development needs to be successfully optimized such as selection of suitable dose, suitable dosage form, suitable route of administration, suitable dosing regimen, effect in animals and humans Thus, there is an unmet need to provide an effective drug delivery system of an β3-adrenergic receptor agonist such as mirabegron.

Mirabegron is soluble in water between neutral to acidic pH. Moreover, the bioavailability of mirabegron is affected by the presence of food in the GI (Gastro-Intestinal) tract. Therefore, to prevent this food effect, the commercially available pharmaceutical formulations of mirabegron are in the form of extended-release tablet formulation based on an orally controlled absorption system (OCAS®) technology. These properties of mirabegron may pose multiple challenges for formulation scientists in the dosage forms development. Moreover, the use of oral dosage form in the treatment of obesity and its related metabolic disorders may not be a suitable approach due to a number of factors such as frequent dosage administration, long treatment period, patient compliance, and low bioavailability.

The bioavailability of the β3-adrenergic receptor agonists can be improved via the injectable route of administration, more particularly a long-acting (extended or sustained release) injectable formulation may provide a higher level of bioavailability after intramuscular or subcutaneous administration than the oral route.

U.S. Patent Publication No. 2018/0326080 assigned to Purdue Research Foundation discloses the utilization of novel polymer-based systems that allow controlled generation of brown/beige adipose tissues for the treatment of obesity and diabetes. This publication also discloses making a microsphere polymer-based drug delivery system via combining a drug with a polymer matrix system. However, the said patent publication fails to exemplify any long-acting injection composition of mirabegron.

In addition to the benefits of increased medication compliance attained through the long-acting injection dosage form, an injectable formulation may also increase the bioavailability of β3-adrenergic receptor agonists particularly mirabegron. The increase in bioavailability of an injectable formulation can provide therapeutic plasma concentration levels with a dose that can be administered intramuscularly or subcutaneously daily, once in every three days, weekly, once in two weeks, once in three weeks, monthly, once in two months, once in three months or once in six months. The total injected dose can be considerably lower than the oral daily dose required over the same time period, thus reducing toxicity and improving patient compliance.

Therefore, in view of the advantages associated with long-acting formulations, there is an unmet need to develop long-acting parenteral formulations of mirabegron, which would provide a higher compliance rate along with maintaining therapeutic levels of the drug in the patient's system for a long period of time (days, weeks, months, or even years) for the treatment of obesity and its related metabolic disorders or diseases as described herein.

SUMMARY OF THE INVENTION

The present invention relates to long-acting parenteral compositions of β3-adrenergic receptor agonists and the process for preparing such compositions.

The present invention further relates to long-acting parenteral compositions of mirabegron or its pharmaceutically acceptable salts or esters thereof such as mirabegron palmitate and the process for preparing such compositions.

The present invention also relates to long-acting parenteral compositions comprising mirabegron or its pharmaceutically acceptable salts or esters thereof and at least one or more pharmaceutically acceptable excipients selected from the group consisting of solvent, emulsifying agent or amphiphilic agent, suspending agent, co-solvent, oil, solubilizing agent, wetting agent, thickening agent, tonicity adjusting agent, pH adjusting agent, preservative, antioxidant, dispersing agent, polymer, lipid and surface modifier.

The present invention also relates to the use of the therapeutically effective amount of long-acting parenteral compositions of mirabegron in the manufacture of a medicament for treating obesity and its related metabolic disorders, hypertension, diabetes, patients at risk of having diabetes (pre-diabetes), cardiovascular diseases, hyperglycemia, gallbladder diseases and even some types of cancer and other diseases also as described herein.

DETAILED DESCRIPTION

As used herein, the term "β3-adrenergic receptor agonist", "β3-adrenoreceptor agonists" or "beta-3 adrenergic receptor agonist" includes compounds such as mirabegron, vibegron, solabegron. Preferably, the compound is mirabegron. "Mirabegron" is used in a broad sense to include not only mirabegron per se (free base) but also its pharmaceutically acceptable salts, solvates, esters, hydrates, enantiomers, derivatives, isomers, stereoisomers, diastereomers, metabolites, polymorphs, and prodrugs thereof. Polymorph may refer to various crystalline and amorphous forms of mirabegron.

As used herein, the pharmaceutically acceptable salt(s) include, but are not limited to, maleic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, fumaric, benzoic, ascorbic, embonic, succinic, oxalic, bismethylenesalicylic, methanesulfonic, ethanedisulfonic, acetic, propionic, tartaric, salicylic, 8-halotheophyllines (e.g. 8-bromo-theophylline), hydrochloric, hydrobromic, sulfuric, sulfamic, phosphoric and nitric acids and the like.

As used herein, the pharmaceutically acceptable ester(s) include, but are not limited to, fatty acid ester including deconate, undecanoate, dodecanoate (lauric), tridecanoate, tetradecanoate (myristic), pentadecanoate, hexadecanoate, palmitate, lactate, heptadecanoate, octadecanoate (stearic), nonadecanoate, oleate, and eicosanoate and alkyl ester including methyl, ethyl, propyl, isopropyl, butyl and the like. Preferably, mirabegron is in the form of mirabegron palmitate, which is a palmitate ester of mirabegron.

As used herein, the term "composition", "formulation", "dosage form" as in pharmaceutical composition, is intended to encompass a drug product comprising mirabegron or its esters, and other inert ingredient(s) (pharmaceutically acceptable excipients). Such pharmaceutical compositions are synonymous with "formulation", "parenteral composition" "injectable composition", "injection composition" and "dosage form" and are used synonymously throughout the application.

The term "parenteral" or "injection" or "injectable" as used herein refers to routes selected from subcutaneous (SC), intravenous (IV), intramuscular (IM), intradermal (ID), intraperitoneal (IP), depot injection, or via an implantable pump, and the like. Transcutaneous is also contemplated as a route of delivery for the pharmaceutical compositions as per present invention. The formulations according to an aspect of the application may be in the form of lyophilized powders, liquid concentrates, ready-to-dilute, and/or ready-to-use solutions. The term "ready-to-dilute" refers to any preparation which is ready for dilution using water, water for injection, dextrose solution, saline solution, or any other infusion medium for administration to the patient. The term "ready-to-use" refers to any preparation which is ready to be administered to the patient directly without any further dilution or processing.

The compositions as per the present invention include injection preparations, such as liquid dosage forms (liquids, liquid dispersions, solutions, suspensions, emulsions), gels, colloids, dry powder, implants, biodegradable or non-biodegradable microparticles/microspheres in the form of controlled-release formulations, lyophilized formulations, delayed-release formulations, extended-release formulations, sustained-release formulations, pulsatile release formulations, and mixed immediate release and controlled release formulations. In certain non-limiting embodiments, the composition is suspension dosage form for parenteral administration. In certain non-limiting embodiments, the composition is a micro-suspension dosage form for parenteral administration. In certain non-limiting embodiments, the composition is a nano-suspension dosage form for parenteral administration.

The term "long-acting" as used herein refers to a pharmaceutical injection formulation that provides prolonged, sustained or extended-release of the mirabegron to the systemic circulation of a subject or local sites of action in a subject. In some embodiments, the release of a drug will take place over a period greater than about 1 day, greater than about 2 days to 6 months, 1 year. In some embodiments, the release of a drug will occur over a period of about 1 month to about 6 months.

The term "excipient" means one or more pharmacologically inactive components comprising one or more of solvents, emulsifying agents or amphiphilic agents, suspending agents, co-solvents, oils, solubilizing agents, wetting agents, thickening agents, tonicity adjusting agents, pH stabilizers/adjusting agents, preservatives, antioxidants, dispersing agents, polymers, lipids, surface modifiers and combination thereof.

The term "overweight", as used herein, refers to an adult individual having a body mass index (BMI) greater than or equal to 24 and less than 27. The term "obese", as used herein, refers to an adult individual having a body mass index (BMI) of greater than or equal to 30.

Unless otherwise stated the weight percentages expressed herein are based on the final weight or volume of the composition or formulation. As used herein, the term "about" means ±approximately 20% of the indicated value, such that "about 10 percent" indicates approximately 08 to 12 percent.

The term "stable" refers to any preparation of mirabegron having sufficient stability to allow storage at a convenient temperature, such as between about 0° C. and about 60° C., for a pharmaceutically acceptable duration of time, preferable at 40° C. and 75% relative humidity (R.H.) or at 25° C. and 60% R.H. Preferably, the compositions are stable for a period of time, such as at least about one week, at least about one month, at least about three months, at least about six months, at least about one year, or at least about 2 years. The purity of mirabegron in compositions as per the present invention ranges from at least 99.99%, 99%, 98%, 97%, 96%, or 95%.

The pharmaceutical compositions of the present invention comprise mirabegron or its salts or esters from about 0.05 μg to 500 mg per day. In some embodiments, the dose of mirabegron or its salts or esters ranges from 0.05 μg to about 200 mg per day, from 0.05 μg to about 100 mg per day, 0.05 μg to about 50 mg per day, 0.05 μg to about 10 mg per day, 0.05 μg to about 5 mg per day, and/or 0.05 μg to about 1 mg per day. In one embodiment, the composition comprises mirabegron palmitate equivalent to 50 mg/ml of mirabegron freebase.

In another preferred embodiment, the present invention provides a pharmaceutical composition comprising mirabegron at concentrations about 0.001 mg/mL to about 200 mg/mL. Typically, the concentrations of mirabegron are in the range of about 10 mg/mL to about 100 mg/mL in some embodiments, the mirabegron is present at a concentration of about 50.0 mg/mL. In other embodiments, the mirabegron is present at a concentration of about 25.0 mg/mL. In other embodiments, the mirabegron is present at a concentration of about 10.0 mg/mL. In other embodiments, the mirabegron is present at a concentration of about 5.0 mg/mL. In other embodiments, the mirabegron is present at a concentration of about 1.0 mg/mL or even less.

The present invention relates to long-acting parenteral pharmaceutical compositions (e.g., lyophilized and/or aqueous compositions) comprising β3-adrenergic receptor agonists such as mirabegron or their salts or esters and methods of use thereof.

The compositions can be lyophilized (e.g., as a powder) for long-term storage. The lyophilized formulations can be reconstituted as biocompatible formulations for administration to a subject in need thereof. In certain non-limiting embodiments, the composition is formulated as a liquid. In certain non-limiting embodiments, the composition is formulated as a liquid suspension for parenteral administration.

The present invention also relates to the long-acting parenteral composition of β3-adrenergic receptor agonists and at least one or more pharmaceutically acceptable excipients and processes for preparing such compositions.

In one embodiment, the present invention further relates to the long-acting injection composition of mirabegron or its pharmaceutically acceptable salts or esters thereof and at least one or more pharmaceutically acceptable excipients.

In another embodiment, the present invention provides a process of preparing long-acting injection composition comprising mirabegron or its salts or esters and at least one or more pharmaceutically acceptable excipients.

In certain non-limiting embodiments, the present invention relates to a long-acting injection suspension composition comprising mirabegron or its salts or esters and at least one or more pharmaceutically acceptable excipients.

In another embodiment, the invention provides a long-acting injection composition comprising: a) mirabegron or its pharmaceutically acceptable salts or esters, and b) a pharmaceutically acceptable vehicle or carrier.

In another embodiment, the present invention further relates to a long-acting injectable composition of mirabegron or its salts or esters, dispersed in a non-aqueous liquid vehicle. In another embodiment, the present invention further relates to a long-acting injectable composition of mirabegron or its salts or esters, dispersed in an aqueous liquid vehicle.

In another embodiment, the present invention relates to a long-acting injectable composition of mirabegron or its salts or esters based on PLGA microsphere technology.

In another embodiment, the present invention also relates to, long-acting injection composition comprising mirabegron or its pharmaceutically acceptable salts or esters thereof and at least one or more pharmaceutically acceptable excipients selected from the group consisting of solvent, emulsifying agent or amphiphilic agent, suspending agent, co-solvent, oil, solubilizing agent, wetting agent, thickening agent, tonicity adjusting agent, pH adjusting agent, preservative, antioxidant, dispersing agent, polymer, lipid, and surface modifier.

In another embodiment of the invention, there is provided a long-acting suspension pharmaceutical composition suitable for parenteral administration comprising: a) mirabegron or its pharmaceutically acceptable salts or esters thereof, b) one or more pH adjusting agents, and c) one or more parenteral solvents.

In another embodiment of the invention, there is provided a long-acting suspension pharmaceutical composition suitable for parenteral administration comprising: a) mirabegron or its pharmaceutically acceptable salts or esters thereof, b) one or more pH adjusting agents, c) wetting agent, and d) one or more parenteral solvents.

In another embodiment of the invention, there is provided a long-acting suspension pharmaceutical composition suitable for parenteral administration comprising: a) mirabegron or its pharmaceutically acceptable salts or esters thereof, b) one or more pH adjusting agents, c) wetting agent, d)

suspending agent, e) dispersing agent, f) tonicity adjusting agent, g) preservative and h) one or more parenteral solvents.

In another embodiment of the invention, there is provided a long-acting pharmaceutical composition suitable for parenteral administration comprising: a) mirabegron or its pharmaceutically acceptable salts or esters thereof; and b) one or more pH adjusting agents; wherein the pH of the composition is about 3.0 to about 8.0.

In another embodiment of the invention, there is provided a long-acting pharmaceutical composition suitable for parenteral administration comprising: a) mirabegron or its pharmaceutically acceptable salts or esters thereof; b) one or more pH adjusting agents; and c) one or more suspending agents; wherein the pH of the composition is about 3.0 to about 8.0.

In another embodiment of the invention, there is provided a long-acting suspension pharmaceutical composition suitable for parenteral administration comprising: a) mirabegron or its pharmaceutically acceptable salts or esters thereof, b) one or more pH adjusting agents, and c) one or more parenteral solvents, wherein the pH of the composition is about 3.0 to about 8.0.

In another embodiment of the invention, there is provided a long-acting pharmaceutical composition suitable for parenteral administration comprising: a) mirabegron or its pharmaceutically acceptable salts or esters thereof; b) one or more pH adjusting agents; c) wetting agent; d) suspending agent; and e) one or more parenteral solvents, wherein the average particle size of mirabegron is from 400 nm to 5 μm and the pH of the composition is about 3.0 to about 8.0. In another embodiment of the invention, the pH of the compositions is in the range of about 5.0 to about 7.5.

In another embodiment of the invention, the composition exhibits at least 10% drug release in about 1 hour, at least 30% drug release in about 3 hours, at least 45% drug release in about 5 hours, at least 55% drug release in about 18 hours and at least 60% drug release in about 24 hours when measured in 500 ml of Phosphate buffer, pH 6.8 using USP II apparatus (Paddle) at a temperature of 37±0.5° C. and a rotation speed of 25 revolutions per minute.

In another embodiment of the invention, the solvent is selected from isopropanol, dimethyl sulfoxide, dimethylformamide, dimethylacetamide, glycerol, water, and mixtures thereof.

In another embodiment the long-acting injection composition of mirabegron or its salts or esters includes particle size of mirabegron Active Pharmaceutical ingredient (API), having a particle size distribution such that $D_{90}$ is less than about 200 μm, $D_{50}$ is less than about 100 μm and $D_{10}$ is less than about 50 μm. Preferably, particle size distribution is $D_{90}$ is less than about 100 μm, $D_{50}$ is less than about 70 μm and $D_{10}$ is less than about 30 μm.

In certain non-limiting embodiments, the long-acting injection compositions comprised of mirabegron or its salts or esters having an average particle size from about 10 nm to about 8 μm. Preferably from about 400 nm to about 5 μm. The particle size can be achieved by any well-known particle size reduction processes, such as sifting, milling, micronization, fluid energy milling, media milling, ball milling, milled through the homogenizer/high-pressure homogenizer, air-jet milling, and the like. The particle size can be measured by suitable techniques such as Laser light scattering (e.g. Malvern Light Scattering), Dynamic light scattering method (Zetasizer equipment), Coulter counter, microscopy, photon correlation spectroscopy, and any other technique known in the art.

In another embodiment, the particle size of mirabegron or its salts or esters formulated in the aqueous suspension of the present invention is in the range from 10 to 8000 nanometers, preferably in the range from 10 to 5000 nanometers, more preferably in the range from 10 to 800 nanometers. Preferably, the average particle size is below 5 microns. In another embodiment, the particle size of solids particles in suspension compositions as per the present invention is in the range from 400 nm to 8 μm. Preferably in the range from 400 nm to 5 μm. The desired particle size of compositions can be achieved by homogenization.

In an embodiment, the amount of mirabegron or its salts or esters in the composition of the present invention is from about 0.0001% to about 90% of the total injection composition. In a preferred embodiment, the amount of mirabegron or its salts or esters in the composition of the present invention is about 0.001% to about 40% of the total composition.

In another embodiment, the present invention is directed to a long-acting injection composition comprising: a) from about 0.001% to about 80% of mirabegron or its pharmaceutically acceptable salts or esters as an active pharmaceutical ingredient and b) about 10% to about 99% of a liquid carrier.

In another embodiment of the invention, the long-acting injection composition comprising: a) from about 1% to about 80% of mirabegron or its pharmaceutically acceptable salts or esters thereof; and b) from 0 to about 80% of one or more oil selected from sesame oil, olive oil, and soybean oil.

In another embodiment of the invention, the long-acting injection of mirabegron comprising: a) from about 1% to about 80% of mirabegron or its pharmaceutically acceptable salts or esters; b) from 0 to about 30% of one or more amphiphilic agents; c) from 0 to about 30% of one or more pH modifiers; d) from 0 to 40% about of one or more suspending agents; e) one or more solvent; and optionally; and f) one or more other pharmaceutically acceptable excipients.

In another embodiment of the invention, the long-acting injection of mirabegron comprising: a) from about 1% to about 70% of mirabegron or its pharmaceutically acceptable salts or esters; b) from about 1% to about 30% of one or more amphiphilic agent; c) from about 1% to about 30% of one or more pH modifier; d) from about 1% to 40% about of one or more suspending agent; e) one or more solvent; and optionally; and f) one or more other pharmaceutically acceptable excipients.

In another embodiment of the invention, there is provided a liquid pharmaceutical composition suitable for parenteral administration comprising: a) about 0.001% to about 80% of mirabegron or its pharmaceutically acceptable salts or esters thereof; b) 0 to about 20% of one or more suspending agents; c) 0 to about 20% of one or more dispersing agents; d) 0 to about 80% of one or more pH adjusting agents; e) 0 to about 30% of one or more wetting agents; f) 0 to about 30% of one or more tonicity adjusting agents; g) 0 to about 20% of one or more preservatives; h) 0 to about 20% of one or more antioxidants; and i) one or more parenteral solvents.

In another embodiment of the invention, there is provided a liquid pharmaceutical composition suitable for parenteral administration comprising: a) about 0.001% to about 80% of mirabegron or its pharmaceutically acceptable salts or esters thereof; b) about 0.01% to about 20% of one or more suspending agents; c) about 0.01% to about 80% of one or more pH adjusting agents; d) 0 to about 30% of one or more wetting agents; and e) one or more parenteral solvents.

In another embodiment of the invention, there is provided a liquid pharmaceutical composition suitable for parenteral administration comprising: a) about 0.001% to about 40% of mirabegron or its pharmaceutically acceptable salts or esters thereof; b) about 0.01% to about 10% of one or more suspending agents; c) about 0.01% to about 20% of one or more pH adjusting agents; d) about 0.01% to about 10% of one or more wetting agents; and e) one or more parenteral solvents.

In another embodiment of the invention, there is provided a long-acting pharmaceutical composition suitable for parenteral administration comprising: a) about 0.001% to about 20% of mirabegron or its pharmaceutically acceptable salts or esters thereof; b) about 0.01% to about 3% of one or more suspending agents; c) about 0.01% to about 5% of one or more pH adjusting agents; d) about 0.01% to about 0.5% of one or more wetting agents; and e) one or more parenteral solvents.

In another embodiment of the invention, one or more pH adjusting agents are selected from the group consisting of inorganic acids, organic acids, inorganic bases, organic bases, borate buffers, acetate buffers, tartrate buffers, lactate buffers, citrate buffers, phosphate buffers, citric acid/phosphate buffers, carbonate/carbonic acid buffers, succinate/succinic acid buffers, ammonium buffers and combinations thereof.

In a certain non-limiting embodiment, the composition further comprises from about 0.01% to about 2% of one or more tonicity adjusting agents. In a certain non-limiting embodiment, the composition further comprises from about 0.01% to about 1% of one or more preservatives.

In another embodiment of the invention, there is provided a liquid pharmaceutical composition suitable for parenteral administration comprising: a) about 0.001% to about 20% of mirabegron or its pharmaceutically acceptable salts or esters thereof; b) about 0.01% to about 3% of one or more suspending agents selected from the group consisting of hydroxypropyl cellulose, hydroxypropyl ethylcellulose, methylcellulose, sodium carboxymethyl cellulose, and hydroxypropyl methylcellulose; c) about 0.01% to about 5% of one or more pH adjusting agents selected from the group consisting of sodium phosphate, citric acid, sodium citrate, glacial acetic acid, hydrochloric acid; d) about 0.01% to about 0.5% of one or more wetting agents selected from the group consisting of sodium lauryl sulphate, polysorbate, and poloxamer, and e) one or more parenteral solvents.

In certain non-limiting embodiments, the composition further comprises from about 0.01% to about 1.5% of one or more dispersing agents selected from the group consisting of carbomers, polyvinyl alcohol, polyvinyl pyrrolidone and xanthan gum.

In certain non-limiting embodiments, the composition further comprises from about 0.01% to about 2% of one or more tonicity adjusting agents selected from the group consisting of, sodium acetate, sodium chloride, dextrose, sodium lactate, calcium chloride, sodium bicarbonate, and potassium chloride.

In certain non-limiting embodiments, the composition further comprises from about 0.01% to about 1% of one or more preservatives selected from the group consisting of methylparaben, propylparaben, benzalkonium chloride, benzyl alcohol, and sodium benzoate.

In another embodiment of the invention, there is provided a liquid pharmaceutical composition suitable for parenteral administration comprising mirabegron or its pharmaceutically acceptable salts or esters thereof, sodium carboxymethylcellulose, sodium phosphate, and polysorbate 80. In an embodiment, the composition further comprises povidone, sodium chloride, and benzyl alcohol.

In another embodiment of the invention, the pharmaceutical composition comprises: mirabegron or its pharmaceutically acceptable salts or esters thereof at a concentration of from 10 mg/ml to about 50.0 mg/mL, polysorbate 80 at a concentration of about 0.01 to 5 mg/mL, one or more pH adjusting agents, and water; wherein the pH of the composition is about 3.0 to about 8.0.

In another embodiment of the invention, the weight ratio of mirabegron to the said suspending agent is 10:0.001 to 0.001:10. Preferably, the weight ratio of mirabegron to the said suspending agent is 10:0.01 to 0.01:10.

In another embodiment of the invention, the weight ratio of mirabegron to the said wetting agent is 10:0.001 to 0.001:10. Preferably, the weight ratio of mirabegron to the said wetting agent is 10:0.01 to 0.01:10. Preferably, the weight ratio of mirabegron to the said wetting agent is 5:0.1 to 0.1:5.

In another embodiment of the invention, the weight ratio of mirabegron to the said tonicity adjusting agent is 10:0.001 to 0.001:10. Preferably, the weight ratio of mirabegron to the said tonicity adjusting agents is 10:0.01 to 0.01:10.

In another embodiment of the invention, the pH adjusting agent is present in the composition in a concentration of about 0.001 mg/ml to about 50 mg/ml. Preferably, from about 0.01 mg/ml to about 20 mg/ml. In another embodiment of the invention, the suspending agent is present in the composition in a concentration of about 0.001 mg/ml to about 20 mg/ml. In another embodiment of the invention, the wetting agent is present in the composition in a concentration of about 0.001 mg/ml to about 5 mg/ml.

In another embodiment of the invention, the long-acting composition is prepared by conventional methods for preparation in the art, including but not limited to, mixing, freeze-drying, spray-drying method, solvent-volatilizing method, emulsion-solvent volatilization, sterile filtration, recrystallization followed by aseptic micronization, dry or wet milling followed by gamma or e-beam irradiation sterilization and atomizing-extracting method.

The methods used for the preparation of the long-acting parenteral compositions as per the present invention may be selected from high shear homogenization, high-pressure homogenization, ultrasonication/high-speed homogenization, an admixture of solvents, solubilizers, and actives to prepare a suspension, solvent emulsification, evaporation and like.

In another embodiment the long-acting injection composition of mirabegron or its salts or esters includes sterilization. Various sterilization procedure includes, but not limited to, heat sterilization, terminal sterilization, dry heat sterilization, moist heat sterilization, filtration, membrane sterilization, radiation or gamma sterilization and the like. After the sterilization injection composition is aseptically packed into a respective container. In alternate embodiments, the composition is terminally sterilized or prepared in strict sterile conditions. In a certain non-limiting embodiment, the composition is sterilized using aseptic filtration. In a certain non-limiting embodiment, the composition is sterilized as: a) aseptic filtration of polymer excipients and sterilization of suspension phase; and b) final mixing of both dispersions followed by filling. In a certain non-limiting embodiment, the composition uses the sterile drug for the preparation of parenteral compositions.

In another embodiment of the invention, the long-acting composition is prepared by dissolving or suspending the mirabegron or its salts or esters in a pharmaceutically acceptable liquid carrier under sterile conditions.

In another embodiment of the invention, the process of preparing long-acting injection composition is carried out under aseptic conditions, and when grinding, the temperature should not exceed 40° C.

In another embodiment of the invention, the long-acting composition is prepared by reconstitution of a sterile freeze-dried preparation comprising: a) mirabegron or its pharmaceutically acceptable salts or esters; and b) one or more pharmaceutically acceptable carrier and/or excipients.

In one embodiment, the invention relates to a process for preparing a long-acting injection composition comprising: a) preparing a first sterile solution comprising one or more pharmaceutically acceptable excipients; b) preparing a second sterile solution comprising mirabegron or its salts or esters; and c) dispersing both solution to form the final sterile composition.

In one embodiment, the invention relates to a process for preparing an injection composition comprising: a) collecting the suitable vehicle (such as water for injection) in a suitable container; b) preparing a dispersion of polymer-based excipients (such as sodium carboxymethyl cellulose, povidone or like) with stiffing for a suitable time at appropriate processing temperature (such as 2-60° C.); c) adding suitable excipients (such as a wetting agent, tonicity adjusting agent, preservative, antioxidant) with stirring for a suitable time; d) adding the drug to the dispersion of step c) with stirring for a suitable time; e) stirring the solution of step d) for a suitable time and adjusting the pH using one or more suitable pH adjusting agents; and f) making the volume up to final batch size using water for injection.

In certain non-limiting embodiments, the process further comprises filtrating the solution using suitable filters (such as 0.2-micron size), filling the solution in appropriate size vials, stoppering the vials using rubber stoppers, and capping the vials using suitable seals (such as aluminum flip-off seals). In certain non-limiting embodiments, the process further comprises sterilizing the composition with suitable sterilization methods (such as terminal sterilization), filling the solution in appropriate size vials, stoppering the vials using rubber stoppers, and capping the vials using suitable seals (such as aluminum flip-off seals).

In another preferred embodiment of the present invention, the composition is prepared by milling the drug suspension in a high-pressure homogenizer. Milling the suspension in a high-pressure homogenizer can be an iterative process starting, for example from 1000 to 40000 psi pressure.

In certain non-limiting embodiments, the process further comprises homogenizing the prepared dosage form. In certain non-limiting embodiments, the homogenization process is carried out in two phases 1) pre-homogenization and 2) final homogenization.

During formulation development, one of the major challenges was to reduce the particle size of suspension formulations to the desired particle size range, which plays a critical role in the development of long-acting injectable suspension compositions. To accomplish this different homogenization approaches were evaluated by present inventors. The present inventors surprisingly found that when un-micronized API was formulated into suspension composition and homogenized at maximum pressure (about 30000 psi) using a high-pressure homogenizer, this did not yield uniform particle size. Based on the extensive research and series of experiments the present inventors were able to get desired uniform particle size for suspension dosage form by 1) pre-homogenizing the formulation using a high shear homogenizer at about 10000 RPM for a suitable time (10-15 minutes) followed by final homogenization using a high-pressure homogenizer at a pressure of 30000 psi.

In another embodiment, the composition is a sterile composition.

In another embodiment, the composition comprises less than 3 percent of impurities, preferably less than 1 percent, more preferably less than 0.5 percent of impurities. In another embodiment, the impurities present in the compositions during stability studies were detected by high-performance liquid chromatography (HPLC) equipped with a suitable detector (such as UV) operating at a suitable wavelength.

In another embodiment, the composition is free of microbial content during storage.

In certain non-limiting embodiments, the composition is formulated at a pH of between about 1 and about 10, or between about 1 and about 8, or between about 1 and about 7.5. In other non-limiting embodiments, the composition is formulated at a pH of between about 2 and about 10, or between about 4 and about 8, or between about 3 and about 8. In a preferred non-limiting embodiment, the composition is formulated at a pH of between about 2.0 and about 7.5. In another embodiment, the pH of the composition is in the range from pH 4.5 to pH 7.5. In another embodiment of the invention, the pH of the compositions is in the range of about 5.0 to about 7.5.

The pH may be measured by placing a pH meter directly into the liquid formulation, such as a pH meter having been calibrated for the appropriate pH range with standard aqueous buffers. Persons skilled in the art will know of other methods which may be used to measure pH. These ranges are for measurements made at room temperature (20 to 25° C.).

In a further embodiment, the composition has an osmolality that is in the range from 100 to 600 mOsm/kg. In a further embodiment, the composition has an osmolality that is in the range from 100 to 500 mOsm/kg. In a further embodiment, the composition has an osmolality that is in the range from 100 to 400 mOsm/kg. In a further embodiment, the composition has an osmolality equal to and/or less than 350 mOsm/kg.

In another embodiment, the temperatures at which the compositions of the present invention are kept for routine storage, within the period of the pharmaceutical shelf-life of the composition, are preferably between 2° and 8° C.

In some embodiments, the disclosure provides a long-acting injectable formulation as described herein, wherein the composition exhibits at least 10% drug release in about 1 hour, at least 30% drug release in about 3 hours, at least 45% drug release in about 5 hours, at least 55% drug release in about 18 hours and at least 60% drug release in about 24 hours when measured in 500 ml of Phosphate buffer, pH 6.8 using USP II apparatus (Paddle) at a temperature of 37±0.5° C. and a rotation speed of 25 revolutions per minute. In a preferred embodiment, the drug release was determined using HPLC (High-Performance Liquid Chromatography) method.

In another embodiment, the long-acting injection composition has a viscosity of about 0.5 poise to about 50 poise at a shear rate of 1/s at 25° C. In some embodiments, the composition has a viscosity of about 0.5 poise to about 10 poise at a shear rate of 10/s at 25° C.

In some embodiments, the disclosure provides a long-acting injectable formulation as described herein, wherein the ratio of area under the curve (AUC) to the maximum serum concentration of the active pharmaceutical ingredient in the subject ($C_{max}$), is increased significantly relative to a regular-release (i.e., non-long acting) dosage form. For example, the ratio (AUC/$C_{max}$) of the long-acting injectable formulation as described here is increased significantly relative to an immediate release oral dosage form, or an immediate release injectable formulation. By way of example, the AUC/$C_{max}$ of the formulation of the present disclosure using mirabegron as an active pharmaceutical ingredient would be increased significantly relative to the commercially available mirabegron e.g., Myrbetriq®.

In another embodiment, the long-acting injection composition of mirabegron or its salts or esters exhibits desired formulation technical attributes such as particle size, ease of manufacturing, drug sterility, pH, viscosity, drug release, dosage regimen, stability, syringeability, injectability, re-dispersibility, patient compliance, and commercially viable and other requirements also.

In further embodiments, the long-acting injection composition of mirabegron or its salts or esters exhibits desired pharmaceutical technical attributes in following tests such as foreign and particulate matter test, sterility test, bacterial endotoxin test, and package integrity leak test for container-closure integrity.

The injection compositions of the present invention exhibit desired technical characteristics based on tests such as 1) pH: pH is measured by using a pH meter, 2) Sterility Test: It can be carried out by inoculation of a culture medium with the composition. If there is no evidence of microbial growth then the preparation being examined passes the test for sterility, 3) Leakage test: Leakage test is employed to test the package integrity. A leakage test can be done by a dye bath test. The test container is immersed in a dye bath. Vacuum and pressure are applied for some time. The container is removed from the dye bath and washed. The container is then inspected for the presence of dye either visually or utilizing UV spectroscopy, 4) Pyrogen test, 5) Content uniformity, 6) Viscosity, 7) Clarity, 8) Drug release, and 9) Stability.

The injection compositions of the present invention exhibit desired other technical parameters such as syringe-ability, injectability, re-dispersibility, and free from clogging. Syringeability describes the ability of an injectable suspension to pass easily through a hypodermic needle on transfer from a vial prior to injection. It includes characteristics such as ease of withdrawal, clogging and foaming tendencies, and accuracy of dose measurements. The injection compositions of the present invention exhibit desired injectability. Injectability refers to the performance of the suspension during the injection. Injectability includes factors such as pressure or force required for injection, evenness of flow, aspiration qualities, and freedom from clogging. The injection compositions of the present invention are free from clogging. Clogging refers to the blockage of syringe needles while administering a suspension. This may involve a number of factors, such as the injection vehicle, wetting of particles, particle size and distribution, particle shape, viscosity, and flow characteristics of the suspension. The injection compositions of the present invention exhibit desired re-dispersibility. Re-dispersibility is the ability of the suspension to uniformly disperse with minimal shaking after it has stood for some time. It can be problematic for a suspension dosage form that undergoes "caking" upon standing due to the settling of the deflocculated particles. "Caking" refers to a process by which the particles settle down at the bottom and not re-dispersible with moderate shaking to form a nondispersible mass of material. The long-acting parenteral compositions prepared as per the present invention were evaluated and found acceptable wrt above mentioned technical parameters.

In one embodiment, the present invention provides a method of administering injection composition locally, intramuscularly, intravenously, or subcutaneously as described in the present invention. In certain non-limiting embodiments, the composition as per the present invention is suitable for administration into adipose tissue of the said subject.

In one embodiment, the present invention provides a kit comprising: a) a long-acting injection composition of mirabegron or its palmitate ester in a suitable container like a vial, ampoule, syringe, auto-injector, pen (single or multi-compartment), and optionally b) a container comprising a diluent or a solvent for preparing the composition; and c) instructions for preparing and administration of the composition.

In another preferred embodiment, the composition according to the invention is adapted for systemic administration.

In another embodiment, the injection composition of mirabegron is intended for use as a single dose. In another embodiment, the injection composition of mirabegron is intended for use in multiple doses.

In an embodiment, the composition as per the present invention is packed in a suitable container selected from a vial, ampoule, syringe, pen (single or multi-compartment), auto-injector, cartridge. In certain non-limiting embodiments, the container includes, but is not limited to, glass vials (for example, but not limited to, flint glass vials), ampoules, plastic flexible containers, for example, but not limited to, PVC (polyvinyl chloride) containers, VisIV™ plastic containers, CR3 elastomer copolyester ether containers, CZ resin containers, polypropylene containers, and syringes.

According to another aspect of the present invention, the invention provides a pharmaceutical kit, wherein the composition comprising a drug and one excipient are contained in a first container, and optionally the suitable solvent or diluent is contained in a second, separate container. In one aspect of the present invention, the composition is directed to a kit comprising a first container selected from a syringe, auto-injector, vial, ampoule, pen, or cartridge, containing at least one excipient and a drug in the appropriate amounts and a second container selected from a syringe, vial, ampoule, auto-injector, pen or cartridge comprising at least one excipient like solvents or diluents. When required, the contents of both containers are combined, for example through a connector or by using male-female syringes and mixed so that the compositions according to the invention are reconstituted, for example by moving forwards and backward the plungers of the syringes.

The prefilled syringes or vials or ampoules or pens or cartridges or auto-injector as per present invention may contain volumes from about 10 ml or less, 5 ml or less, 3 ml or less, 1 ml or less, 0.5 ml or less.

In some embodiments, administration can occur at least daily, once in every three days, weekly, once in two weeks, once in three weeks, monthly, once in two months, once in three months, or once in six months.

In another embodiment, the present invention provides a suitable dosing regimen for administering mirabegron or its esters such as palmitate, to a patient in need of treatment comprising administering intramuscularly or subcutaneous injection with a first loading dose from about 0.05 µg to about 200 mg of mirabegron or mirabegron palmitate formulated in an extended-release formulation on the first day of treatment, administering intramuscularly or subcutaneously a second loading dose from about 0.05 µg to about 150 mg of mirabegron or its esters such as palmitate formulated in an extended-release formulation between about the 5th to 20th day of treatment; and administering a maintenance dose of about 0.05 µg to about 150 mg of mirabegron or mirabegron palmitate in an extended-release formulation approximately administered monthly from the date of the second loading dose.

In another embodiment of the invention, the present invention provides a method for reducing or non-surgical removal of body fat in an individual by administering mirabegron parenteral compositions.

In another embodiment, provided herein are methods for treating regional fat accumulation and/or activating browning of adipose tissue in a patient comprising administering to the patient a long-acting injection composition comprising mirabegron or its pharmaceutically acceptable salts or esters thereof and one or more pharmaceutically acceptable excipients.

In another embodiment of the invention, there is provided a use of a therapeutic effective amount of injection composition of mirabegron or its salts or esters in the manufacture of a medicament for treating overactive bladder, pediatric neurogenic detrusor overactivity (NDO), obesity, and its related metabolic disorders, reduction/removal of localized fat, hypertension, patients at risk of having diabetes (pre-diabetes), diabetes, cardiovascular diseases, hyperglycemia, gallbladder diseases, excess fat on the chin (submental fullness or double chin disorder), binge eating, hypothyroidism, excess fat on the breast, adiposis dolorosa, familial partial lipodystrophies (FPLD), benign symmetric lipomatosis, lipedema, familial lipodystrophy, familial partial lipodystrophy, HIV lipodystrophy, Bardet-Biedl syndrome, hypertrophy of dorsocervical fat/dorsocervical fat hypertrophy ("buffalo hump"), lipoma, lipomatosis, moon facies, Down syndrome, pseudo-Cushing syndrome, Cohen syndrome, Cushing syndrome, Prader-Willi syndrome, Turner syndrome, and/or Madelung disease.

In another embodiment of the invention, there is provided a use of a therapeutic effective amount of injection composition of mirabegron or its salts or esters for treating a condition selected from the group comprising of double chin disorder, benign symmetric lipomatosis, adiposis dolorosa, lipedema, familial partial lipodystrophy.

In an embodiment, the present invention provides pharmaceutical compositions and methods to reduce regional fat, adipose tissue, adipocyte, and regional or localized adiposity.

In an embodiment, the fat is reduced from a body part selected from the group consisting of the abdomen, chin, waist, arm, leg, knee, thigh, chest, breast, neck, face, buttock, lateral buttock, peri-orbital region, intra-orbital region. Injection as per the present invention can be injected into the abdomen, chin, waist, arms, legs, knees, thigh, chest, breast, neck, face, buttocks, lateral buttock, peri-orbital region, intra-orbital region, or to a particular fat deposit area.

In another embodiment of the invention, there is provided a use of the therapeutic effective amount of injection composition for the reduction of submental fat (double chin) in a subject, said method comprising administering about 0.001 mg to about 100 mg of said mirabegron per square centimeter of the skin area over said submental fat.

In another embodiment of the invention, the pharmaceutical composition as per the present invention is administered within a plurality of treatment sessions. In a further embodiment, each treatment session is spaced by at least 1 day. In other embodiment, each treatment session is separated from another treatment session by at least 2 to 30 days. In another embodiment of the invention, a plurality of treatment sessions may include administration of injection composition up to a maximum of 80 injections.

In another embodiment of the invention, a plurality of treatment sessions for double chin disease by injection composition are spaced at least about 0.1 cm apart. In further embodiments, the plurality of treatment sessions by injection composition are spaced from about 0.1 cm to about 10 cm apart. In another embodiment, the plurality of treatment sessions by injection composition are spaced about 0.3 cm apart. In a further embodiment, space is usually measured by a marker to be applied to the affected area of the patient.

Experimental tests for the effect of mirabegron in reducing fat deposition in a subject in need thereof include, Pre-clinical studies including: 1) In-vitro tests, 2) Animal study (effect on inguinal lateral fat pad of hamsters/rats), 3) Clinical studies including: i) In-vivo human study, ii) Body mass index (BMI) study (Quantitative methods for the analysis of weight loss or maintenance include measurements of body mass index (BMI). In some embodiments, BMI may be monitored by determining a subject's body mass and height and then dividing the individual's body mass by the square of their height, with the value given in units of kg/m. BMI values may range from underweight to obesity and may be used to assess how much a subject's body weight departs from what is normal or desirable for a person of his or her height.

The parenteral solvents used in the present invention are non-toxic, biocompatible, and appropriate for injection dosage forms. Various useful solvent(s) or carrier(s) or vehicle(s) or parenteral solvent(s) include, but are not limited to, oils, $C_2$-$C_6$ aliphatic alcohols, ethanol, 1-propanol, 2-propanol, 1-butanol, 2-butanol, 1-pentanol, 2-pentanol, 3-pentanol, isopropanol, benzyl alcohol, glycol ethers (e.g., including, but limited to, diethyleneglycol monoethyl ether (DGME, Transcutol®)), butyl diglycol, dipropylene glycol n-butyl ether, ethyleneglycol monoethyl ether, dipropylene glycol monomethyl ether, propylene glycol monomethyl ether, propylene glycol monoethyl ether, liquid polyethylene glycols (PEGs) (PEG 200, PEG 300, PEG 400), carbonates (e.g., propylene carbonate), 2-pyrrolidone, N-methylpyrrolidone, dimethyl isosorbide, dimethylacetamide, glycerol formal, dichloromethane, chloroform, ethyl acetate, dioxane, ethyl ether, acetone, tetrahydrofuran, benzene, toluene, glacial acetic acid, petroleum ether, alkane, paraffine, dimethylsulfoxide, liquid polyethylene glycol, block copolymers of oxyethylene, polyoxyethylene alcohol, polyoxyethylene fatty acid esters, hydrocarbons, n-propane, n-butane, isobutane, n-pentane, iso-pentane, neo-pentane, n-hexane, ethers, diethyl ether, hydroxylated solvents, dextrose, aqueous saline, water, purified water, water for injection, diethylene glycol ethyl ether, isopropylidene glycerol, glycerol, N-methyl-pyrrolidone, N-pyrrolidone, methylethylketone, 1-dodecylazacycloheptane, dipropyleneglycol methyl ether, methyl acetate, ethyl lactate, dimethylformamide, N,N-diethyl-m-toluamide, ethylacetamide, caprolactam, decylmethylsulfoxide, triacetin and the like and mixtures thereof. Typically, water with the qualification "for injections", as defined in acknowledged Pharmacopoeias, is used. In an embodiment, the solvent according to the present invention is present in an amount of about 99.99% or less, e.g. 90% or less, 80% or less, 70% or less, 60% or less, 50% or less, 40% or less, 30% or less, 20% or less, 10% or less.

Various useful suspending agents or viscosity modifying agents include, but are not limited to, cellulose derivatives, e.g. hydroxypropyl cellulose, hydroxypropyl ethylcellulose, methylcellulose, carboxymethyl cellulose, sodium carboxymethyl cellulose, hydroxypropyl methylcellulose, polyvinylpyrrolidone, alginates, chitosan, dextrans, gelatin, propylene glycol, polyethylene glycols, polyoxyethylene- and polyoxypropylene ethers, or mixtures thereof. Suspending agents as per the present invention can also be used as a surface modifier or as viscosity modifying agents. In an embodiment, the suspending agent according to the present invention is present in an amount of about 40% or less, e.g. 30% or less, 20% or less, 10% or less, 5% or less.

Various useful oil(s) or non-aqueous or lipid vehicle include, but are not limited to, vegetable oil, castor oil, cottonseed oil, olive oil, peanut oil, sesame oil, cottonseed oil, corn oil, light vegetable oil, coconut oil, palm seed oil, ethyl oleate, isopropyl myristate (IPM), pungent/capric acid glyceryl ester, glyceryl triacetate, soybean oil, capric acid monoglyceride, capric acid diglyceride, hydrogenated vegetable oil, safflower oil, and the like thereof. In an embodiment, the oil according to the present invention is present in an amount of about 90% or less.

Various useful wetting agent(s) or surfactant(s) or solubility enhancer(s) or permeation enhancer(s) include, but are not limited to, one or more of anionic, cationic, non-ionic, or zwitterionic surfactants or mixtures thereof such as sodium lauryl sulphate, polysorbate (e.g. polysorbate 20, polysorbate 40, polysorbate 60, and polysorbate 80), cetrimide, cetyl alcohol, stearyl alcohol, cetyl stearyl alcohol, cholesterol, polyethylene glycols, polyglycerin fatty acid esters such as decaglyceryl monolaurate and decaglyceryl monomyristate, sorbitan fatty acid esters (sorbitan monostearate), sodium oleate, polyoxyethylene sorbitan fatty acid esters such as polyoxyethylene sorbitan monooleate, sorbitan monolaurate, polyoxyethylene alkyl ether such as polyoxyethylene lauryl ether, polyoxyethylene castor oil, polyoxyethylene polyoxypropylene block copolymers such as poloxamer (such as poloxamer 124, poloxamer 188, poloxamer 237, poloxamer 338, and poloxamer 407), beta-cyclodextrin, glyceryl monostearate, diethylene glycol monostearate, diethylene glycol monolaurate, polyoxyethylene sorbitol beeswax, polyethylene lauryl ether, polyoxyethylene lauryl ether, polyoxyethylene monostearate, polyoxyethylene alkyl phenol, polyethylene sorbitan monooleate, polyethylene sorbitan monolaurate, polyoxyethylene lauryl ether, potassium oleate, triethanolamine oleate or mixtures thereof. The amount of wetting agent or surfactant or solubility enhancer or permeation enhancer according to the present invention ranges from about 0 to about 50% by weight of the composition. In an embodiment, the solubilizing agent, wetting agent according to the present invention is present in an amount of about 50% or less, e.g. 40% or less, 30% or less, 20% or less, 10% or less, 5% or less.

Various useful tonicity adjusting agent(s) include, but are not limited to, potassium chloride, mannitol, glycerin, lactose, glycerol, dextrose, sodium chloride, sodium sulfate, sorbitol, trehalose, ammonium carbonate, ammonium chloride, ammonium lactate, ammonium nitrate, ammonium phosphate, ammonium sulfate, ascorbic acid, bismuth sodium tartrate, boric acid, calcium chloride, disodium calcium edetate, calcium gluconate, calcium lactate, citric acid, dextrose, diethanolamine, dimethyl sulfoxide, disodium edetate, trisodium edetate monohydrate, sodium fluorescein, fructose, galactose, glycerin, lactic acid, lactose, magnesium chloride, magnesium sulfate, polyethylene glycol, potassium acetate, potassium chlorate, potassium chloride, potassium iodide, potassium nitrate, potassium phosphate, potassium sulfate, propylene glycol, silver acid, sodium acetate, sodium bicarbonate, sodium biphosphate, sodium bisulfite, sodium borate, sodium bromide, sodium cacodylate, sodium carbonate, sodium chloride, sodium citrate, sodium iodide, sodium lactate, metabisulfate sodium sulfite, sodium nitrate, sodium nitrite, sodium phosphate, sodium phosphate monobasic monohydrate, sodium phosphate dibasic anhydrous, sodium propionate, sodium succinate, sodium sulfite, sodium tartrate, sodium thiosulfate, sorbitol, maltose, sucrose, tartaric acid, triethanolamine, urea, urethane, uridine zinc sulfate, zinc chloride, albumin, amino acid alone or in combination thereof. In an embodiment, the tonicity adjusting agent according to the present invention is present in an amount of about 40% or less, e.g. 30% or less, 20% or less, 10% or less, 5% or less.

Various useful pH stabilizer(s) or buffer(s) or pH adjusting agent(s) include, but are not limited to, acetic acid/acetate, sodium acetate, ascorbic acid, gluconate buffer, sodium carbonate, disodium hydrogen phosphate anhydrous, sodium dihydrogen phosphate monohydrate, hydrochloric acid, malic acid/malate, citric acid/citrate, sulfuric acid, nitric acid, phosphoric acid/phosphate, adipic acid, benzoic acid, sodium benzoate, boric acid, potassium phosphate, monobasic sodium acetate, sodium bicarbonate, tris buffer, sodium borate, citric acid, glycine/glycimate, maleic acid, sodium phosphate, sodium phosphate monobasic monohydrate, sodium phosphate dibasic anhydrous, sodium diphosphate, HEPES, lactic acid/lactate, tartaric acid/tartrate, potassium metaphosphate, sodium tartrate, anhydrous sodium citrate, dihydrate and combination thereof. Other buffering agents also include citric acid, citric acid/phosphate mixture, acetate, barbital, borate, Britton-Robinson, cacodylate, collidine, formate, maleate, mclvaine, phosphate, glutamic acid/glutamate, prideaux-ward, succinate, citrate-phosphate-borate (Teorell-Stanhagen), veronal acetate, MES (2-(N-morpholino) ethanesulfonic acid), Bis-Tris (bis (2-Hydroxyethyl) imino-tris (hydroxymethyl) methane), ADA (N-(2-acetamido)-2-iminodiacetic acid), ACES (N-(carbamoylmethyl)-2-aminoethanesulfonic acid), PIPES (piperazine-N, N'-bis (2-ethanesulfonic acid)), MOPSO (3-(N-Morpholino)-2-hydroxypropanesulfonic acid), bistris propane (1,3-bis (tris (hydroxymethyl) methylamino) propane), BES (N, N-bis (2-hydroxyethyl)-2-aminoethane Sulfonic acid), MOPS (3-(N-morpholino) propanesulfonic acid), TES (N-tris (hydroxymethyl) methyl-2-aminoethanesulfonic acid), HEPES (N-(2-hydroxyethyl) piperazine-N'-(2-ethanesulfonic acid), dipso (3-(N, N-bis (2-hydroxyethyl) amino)-2-hydroxypropanesulfonic acid), MOBS (4-(N-morpholino)-butanesulfonic acid), tricine (N-tris (hydroxymethyl)) Methylglycine), GLY-GLY (glycylglycine), bicine (N, N-bis (2-hydroxyethyl) glycine), HEPBS (N-(2-hydroxyethyl) piperazine-N'-(4-butanesulfone) Acid)), TAPS (N-tris (hydroxymethyl) methyl)-3-amino-propanesulfonic acid), AMPD (2-amino-2-methyl-1, 3-propanediol), Tapso (3-(N-tris (hydroxymethyl) methylamino)-2-hydroxy Propanesulfonic acid), Trizma™ (Tris (hydroxymethylaminomethane), Heppso (N-(2-hydroxyethyl) piperazine-N'-(2-hydroxypropanesulfonic acid), popso (piperazine-N,N')-Bis (2-hydroxypropanesulfonic acid)), TEA (triethanolamine), EPPS (N-(2-hydroxyethyl) piperazine-N'-(3-propanesulfonic acid), alone or in combination thereof. In an embodiment, the pH stabilizer according to the present invention is present in an amount of about 40% or less, e.g. 30% or less, 20% or less, 10% or less, 5% or less.

Various useful preservative(s) include, but are not limited to, ethanol, parabens (methylparaben and/or propylparaben), benzalkonium chloride, benzethonium chloride, methyl, ethyl, propyl, and butyl esters of hydrobenzoic acid, benzoic acid, imidura, benzyl alcohol, bronopol, butylparaben, cetrimide, chlorhexidine, chlorobutanol, chlorocresol, cresol, ethylparaben, imidurea, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, m-cresol, phenol, phenylmercuric salts, butylated hydroxyltoluene (BHT), butylated hydroxyanisole (BHA), propyl gallate, tocopherols, DMDM Hydantoin®, Euxyl® K400, Bronopol® (2-bromo-2-nitropropane-1,3-diol), chlorhexidine, 2-phenoxyethanol, chlorbutol, thiomersal and the like and mixtures thereof. In an embodiment, the preservative according to the present invention is present in an amount of about 20% or less, e.g. 10% or less, 5% or less, 2.5% or less.

Various useful antioxidant(s) include, but are not limited to, ascorbic acid and its salts, butylated hydroxytoluene, butylated hydroxyanisole, metal chelators such as ethylenediaminetetraacetic acid, ascorbyl palmitate, benzoic acid, benzyl alcohol, tocopherol, vitamin E, alpha-tocopherol, ascorbyl palmitate, sodium metabisulfite, sodium bisulphite, propyl gallate, n-propyl gallate, methionine, fumaric acid, malic acid, sodium ascorbate, BHA (butylated hydroxyanisole), BHT (butylated hydroxytoluene), citric acid, monothioglycerol, tert-butyl hydroquinone (TBHQ), phenols, and mixtures thereof. In an embodiment, the antioxidant according to the present invention is present in an amount of about 20% or less, e.g. 10% or less, 5% or less, 2.5% or less.

Various useful dispersant(s) or dispersing agent(s) include, but are not limited to, carbomers, polyvinyl alcohol, polyvinyl pyrrolidone, hydroxypropylmethylcellulose, hydroxyethyl cellulose, hydroxypropyl cellulose, low substituted hydroxypropyl cellulose, methylcellulose, carboxymethyl cellulose, carboxymethyl cellulose sodium, cross-linked sodium carboxymethyl cellulose, calcium carboxymethyl cellulose, microcrystalline cellulose, powdered cellulose, xanthan gum, gellan gum, carrageenan, acacia, tragacanth, gelatin, guar gum, alginic acid, sodium alginates, propylene glycol alginate, magnesium aluminum silicate, or a mixture thereof. In an embodiment, the dispersing agents according to the present invention are present in an amount of about 20% or less, e.g. 10% or less, 5% or less, 2.5%, or less.

Various useful polymer(s) include, but are not limited to, the biodegradable polymer includes poly (D, L- or L-lactic acid) (PLA) and poly (glycolic acid) (PGA) and their copolymers (PLGA).

The compositions of the present invention may further comprise one or more other excipients such as emulsifying agents, amphiphilic agents, co-solvents, thickening agents, and lipids. These excipients may present in an amount of about 50% or less.

The following examples are provided to illustrate embodiments of the disclosure but they are by no means intended to limit its scope.

Mirabegron long-acting injection compositions are to be, or were, prepared by using quantitative formula as given in Tables 1-3 under sterile conditions as per processes as mentioned in the present invention and filled into a suitable container (quantity (%) w/w).

TABLE 1

Examples - 1-4

| Ingredients | Quantity (%) | | | |
|---|---|---|---|---|
| | 1 | 2 | 3 | 4 |
| Mirabegron or Mirabegron Palmitate | 1-80 | 1-70 | 73.1 | 50 |
| Polysorbate 20 | 0-30 | 1-20 | 5.6 | 5.6 |
| Citric Acid monohydrate | 0-20 | 1-15 | 2.34 | 2.34 |
| Disodium hydrogen phosphate | 0-20 | 1-20 | 2.34 | 2.34 |
| Sodium dihydrogen phosphate | 0-30 | 1-10 | 1.17 | 1.17 |
| Sodium Hydroxide | 0-30 | 1-20 | 1.33 | 1.33 |
| Polyethylene Glycol 4000 | 0-40 | 1-40 | 14.06 | 14.06 |
| Solvent/Oil | q.s. | q.s. | q.s. | q.s. |

TABLE 2

Examples - 5-9

| Ingredients | Quantity (%) | | | | |
|---|---|---|---|---|---|
| | 5 | 6 | 7 | 8 | 9 |
| Mirabegron or Mirabegron Palmitate | 1-80 | 50 | 20 | 30 | 73.1 |
| Sesame Oil | 0-80 | 50 | — | — | — |
| Olive Oil | 0-80 | — | 80 | — | — |
| Soybean Oil | 0-80 | — | — | 70 | — |
| Vegetable Oil | 0-80 | — | — | — | 26.9 |

TABLE 3

Examples - 10-19

| Ingredients | Quantity (%) | | | | | | | | | |
|---|---|---|---|---|---|---|---|---|---|---|
| | 10 | 11 | 12 | 13 | 14 | 15 | 16 | 17 | 18 | 19 |
| Mirabegron | 0.001-80 | 0.001-30 | 5 | 5 | 5 | 2.5 | 2.5 | 1 | 1 | — |
| Mirabegron palmitate | — | — | — | — | — | — | — | — | — | 5 |
| Sodium phosphate monobasic | 0-20 | 0-5 | 0.38 | — | 0.38 | 0.38 | 0.46 | 0.38 | 0.62 | 0.38 |
| Sodium phosphate dibasic | 0-20 | 0-5 | 0.66 | — | 0.66 | 0.66 | 0.58 | 0.66 | 0.42 | 0.66 |
| Sodium carboxy methyl cellulose | 0-20 | 0-5 | 0.5 | 0.6 | 0.5 | 0.5 | 0.5 | 0.5 | 0.5 | 0.5 |
| Povidone | 0-20 | 0-5 | — | — | — | — | — | — | — | — |
| Sodium Chloride | 0-20 | 0-5 | — | 0.66 | — | — | — | — | — | — |
| Benzyl alcohol | 0-20 | 0-5 | — | 0.9 | — | — | — | — | — | — |
| Polysorbate-80 | 0-20 | 0-5 | — | 0.04 | 0.05 | 0.05 | 0.05 | 0.05 | 0.05 | 0.05 |
| Water for injection | 0-90 | q.s. | q.s. | q.s. | q.s. | q.s. | q.s. | q.s. | q.s. | q.s. |

Procedure: a) suitable vehicle (such as water for injection) was collected in a suitable container; b) dispersion of suitable polymer-based excipients (such as sodium carboxymethyl cellulose, povidone, or like) was prepared with stirring for a suitable time at appropriate processing temperature (such as 2-30° C.); c) suitable excipients (such as a wetting agent, tonicity adjusting agent, preservative, antioxidant) were added with stirring for a suitable time; d) drug was added to the dispersion of step c) with stirring for a suitable time; e) the dispersion of step d) was stirred for a suitable time and the pH was adjusted using one or more suitable pH adjusting agents; f) the volume was made up to final batch size using water for injection. The dispersion of step f) was finally sterilized with a suitable sterilization method (such as terminal sterilization), and filled in appropriate size vials, stoppered the vials using rubber stoppers, and capped the vials using suitable seals. The prepared dispersion was further homogenized at suitable pressure (up to 30000 psi).

Results: The compositions prepared as per Examples 12-18 include mirabegron that are at concentrations within the range of about 0.001 mg/mL to about 50 mg/mL.

Appearance: Upon following the above procedures, the prepared compositions given in Examples 12-18 appeared as white to off-white suspension.

pH: The pH of the compositions prepared according to the quantities of Examples 12-18 was in the range of about 5.0 to about 7.5.

Particle Size: The particle size of the compositions prepared according to the quantities of Examples 12-18 was below 5 μm and accordingly found acceptable.

Drug Release: The compositions prepared according to the quantities given in Examples 14-16 exhibit at least 10% drug release in about 1 hour, at least 30% drug release in about 3 hours, at least 45% drug release in about 5 hours, at least 55% drug release in about 18 hours, and at least 60% drug release in about 24 hours when measured in 500 ml of Phosphate buffer, pH 6.8 using USP II apparatus (Paddle) at a temperature of 37±0.5° C. and a rotation speed of 25 revolutions per minute.

Other Parameters: The injection compositions of the present invention prepared according to the quantities of Examples 12-18 exhibit desired technical parameters such as syringeability, re-dispersibility, and free from clogging.

Based on the results of Examples 12-18 it was determined that suitable injectable formulations of mirabegron include compositions comprising, consisting of, or consisting essentially of (for one or more of syringeability, re-dispersibility, freedom from clogging and stability):

(1) Formulation 1: 5% mirabegron, about 0.38% sodium phosphate monobasic, about 0.66% sodium phosphate dibasic, about 0.5% sodium carboxy methyl cellulose, about 0.05% polysorbate 80, and remaining water for injection;

(2) Formulation 2: 2.5% mirabegron, about 0.38% sodium phosphate monobasic, about 0.66% sodium phosphate dibasic, about 0.5% sodium carboxy methyl cellulose, about 0.05% polysorbate 80, and remaining water for injection;

(3) Formulation 3: 2.5% mirabegron, about 0.46% sodium phosphate monobasic, about 0.58% sodium phosphate dibasic, about 0.5% sodium carboxy methyl cellulose, about 0.05% polysorbate 80, and remaining water for injection;

(4) Formulation 4: 1% mirabegron, about 0.38% sodium phosphate monobasic, about 0.66% sodium phosphate dibasic, about 0.5% sodium carboxy methyl cellulose, about 0.05% polysorbate 80, and remaining water for injection;

(5) Formulation 5: 1% mirabegron, about 0.62% sodium phosphate monobasic, about 0.42% sodium phosphate dibasic, about 0.5% sodium carboxy methyl cellulose, about 0.05% polysorbate 80, and remaining water for injection; and (6) Formulation 6: 1-5% mirabegron, about 0.38-0.62% sodium phosphate monobasic, about 0.42-0.66% sodium phosphate dibasic, about 0.5% sodium carboxy methyl cellulose, about 0.05% polysorbate 80, and remaining water for injection.

What is claimed:

1. A sterile, suspension of mirabegron or its pharmaceutically acceptable esters selected from the group consisting of decanoate, undecanoate, palmitate, and lactate, in the form of a long-acting pharmaceutical composition suitable for parenteral administration comprising:
   a) about 0.001% to about 20% w/w of mirabegron or its pharmaceutically acceptable esters thereof;
   b) about 0.01% to about 5% w/w of one or more pH adjusting agents selected from the group consisting of sodium phosphate, citric acid, sodium citrate, glacial acetic acid, and hydrochloric acid and being present in an amount to provide a pH of the composition in the range of about 5.0 to about 7.5;
   c) about 0.01% to about 0.5% w/w of one or more suspending agents selected from the group consisting of hydroxypropyl cellulose, hydroxypropyl ethylcellulose, methylcellulose, sodium carboxymethyl cellulose, polyvinylpyrrolidone, and hydroxypropyl methylcellulose;
   d) about 0.01% to about 0.5% w/w of one or more wetting agents selected from the group consisting of sodium lauryl sulphate, polysorbate, and poloxamer;
   e) about 0.01% to about 2% w/w of one or more tonicity adjusting agents selected from the group consisting of sodium acetate, sodium chloride, dextrose, sodium lactate, calcium chloride, sodium bicarbonate, and potassium chloride present in an amount to provide an osmolality of from about 100 to about 400 mOsm/kg; and
   f) one or more parenteral solvents;
   wherein the pH of the composition is about 5.0 to about 7.5, the osmolality is about 100 to about 400 mOsm/kg and the weight ratio of mirabegron to suspending agent is about 1:0.1 to 1:0.5, the average particle size of mirabegron in the composition is from 400 nm to 5 μm and wherein the composition exhibits at least 10% release of the mirabegron or its ester in 1 hour, at least 30% release of the mirabegron or its ester in 3 hours, at least 45% release of the mirabegron or its ester in 5 hours, at least 55% release of the mirabegron or its ester in 18 hours and at least 60% release of the mirabegron or its ester in 24 hours when measured in 500 ml of Phosphate buffer, pH 6.8 using USP II apparatus (Paddle) at a temperature of 37±0.5° C. and a rotation speed of 25 revolutions per minute.

2. The composition according to claim 1, further comprising one or more pharmaceutically acceptable excipients selected from the group consisting of emulsifying agent, co-solvent, oil, solubilizing agent, thickening agent, preservative, antioxidant, dispersing agent, polymer, lipid, and surface modifier.

3. The composition according to claim 1, wherein the parenteral solvent is selected from the group consisting of isopropanol, dimethyl sulfoxide, dimethylformamide, dimethylacetamide, glycerol, water, and mixtures thereof.

4. The composition according to claim 1, wherein the composition comprises:
   about 1-5% w/w mirabegron;
   about 0.38-0.62% w/w sodium phosphate monobasic;
   about 0.42-0.66% w/w sodium phosphate dibasic;
   about 0.5% w/w sodium carboxymethyl cellulose;
   about 0.05% w/w polysorbate 80; and
   water for injection.

5. The composition according to claim 1, wherein the composition further comprises from about 0.01% to about 1% w/w of one or more preservatives.

6. The composition according to claim 5, wherein the one or more preservatives are selected from the group consisting of methylparaben, propylparaben, benzalkonium chloride, benzyl alcohol, and sodium benzoate.

7. A sterile, suspension of mirabegron in the form of a long-acting liquid pharmaceutical composition suitable for parenteral administration consisting of:
   a. about 1% to about 5% w/w of mirabegron or an ester thereof, wherein the mirabegron or its ester is in solid particle form suspended in the liquid pharmaceutical composition and having an average particle size of from 400 nm to 5 µm;
   b. about 0.01% to about 5% w/w of one or more pH adjusting agents selected from the group consisting of sodium phosphate, citric acid, sodium citrate, glacial acetic acid, and hydrochloric acid and being present in an amount to provide a pH of the composition in the range of about 5.0 to about 7.5;
   c. about 0.01% to about 0.5% w/w of one or more suspending agents selected from the group consisting of hydroxypropyl cellulose, hydroxypropyl ethylcellulose, methylcellulose, sodium carboxymethyl cellulose, polyvinylpyrrolidone, and hydroxypropyl methylcellulose;
   d. about 0.01% to about 0.5% w/w of one or more wetting agents selected from the group consisting of sodium lauryl sulphate, polysorbate, and poloxamer;
   e. about 0.01% to about 2% w/w of one or more tonicity adjusting agents selected from the group consisting of sodium acetate, dextrose, sodium lactate, calcium chloride, sodium bicarbonate, and potassium chloride present in an amount to provide an osmolality of from about 100 to about 400 mOsm/kg; and
   f. one or more parenteral solvents;
   wherein the composition has an osmolality of about 100 to about 400 mOsm/kg and the weight ratio of mirabegron to suspending agent of about 1:0.1 to 1:0.5.

8. A sterile, suspension of mirabegron in the form of a long-acting liquid pharmaceutical composition suitable for parenteral administration consisting of:
   a. about 1% to 5% w/w of mirabegron or its palmitate ester suspended in the liquid pharmaceutical composition and having an average particle size of from 400 nm to 5 µm;
   b. about 0.38 to 0.62% w/w sodium phosphate monobasic;
   c. about 0.42 to 0.66% w/w sodium phosphate dibasic;
   d. about 0.5% to 0.6% w/w of one or more suspending agents selected from the group consisting of sodium carboxymethyl cellulose and polyvinylpyrrolidone,
   e. about 0.04% to 0.05% w/w of polysorbate; and
   f. water for injection;
   wherein pH of the composition is in the range of about 5.0 to about 7.5 and the composition has an osmolality of about 100 to about 400 mOsm/kg and weight ratio of mirabegron to suspending agent of about 1:0.1 to 1:0.5.

9. The composition of claim 8, wherein the composition exhibits at least 10% release of the mirabegron or its palmitate ester in 1 hour, at least 30% release of the mirabegron or its palmitate ester in 3 hours, at least 45% release of the mirabegron or its palmitate ester in 5 hours, at least 55% release of the mirabegron or its palmitate ester in 18 hours and at least 60% release of the mirabegron or its palmitate ester in 24 hours when measured in 500 ml of Phosphate buffer, pH 6.8 using USP II apparatus (Paddle) at a temperature of 37±0.5° C. and a rotation speed of 25 revolutions per minute.

10. The composition of claim 1, wherein the one or more suspending agents is present at 0.5% w/w.

11. A method for reducing or non-surgical removal of body fat in an individual, the method comprising administering to the individual the composition according to claim 1.

12. A method for reducing or non-surgical removal of body fat in an individual, the method comprising administering to the individual the composition according to claim 7.

13. A method for reducing or non-surgical removal of body fat in an individual, the method comprising administering to the individual the composition according to claim 8.

* * * * *